(12) United States Patent
Fiering

(10) Patent No.: US 9,645,060 B2
(45) Date of Patent: May 9, 2017

(54) APPARATUS AND METHOD FOR SEPARATING PLASMA FROM BLOOD AND DELAYED WETTING

(71) Applicant: The Charles Stark Draper Laboratory, Inc., Cambridge, MA (US)

(72) Inventor: Jason O. Fiering, Boston, MA (US)

(73) Assignee: THE CHARLES STARK DRAPER LABORATORY, INC., Cambridge, MA (US)

(*) Notice: Subject to any disclaimer, the term of this patent is extended or adjusted under 35 U.S.C. 154(b) by 0 days.

(21) Appl. No.: 14/499,643

(22) Filed: Sep. 29, 2014

(65) Prior Publication Data
US 2015/0017737 A1    Jan. 15, 2015

Related U.S. Application Data

(62) Division of application No. 13/679,620, filed on Nov. 16, 2012, now Pat. No. 8,900,532.

(51) Int. Cl.
*G01N 33/50*    (2006.01)
*G01N 1/40*    (2006.01)
(Continued)

(52) U.S. Cl.
CPC .......... *G01N 1/4055* (2013.01); *B01D 21/00* (2013.01); *B01L 3/502738* (2013.01); *B01L 3/502753* (2013.01); *B04B 11/04* (2013.01); *G01N 33/491* (2013.01); *B01L 2300/0825* (2013.01); *B01L 2300/165* (2013.01); *B01L 2400/0406* (2013.01); *B01L 2400/0409* (2013.01); *B01L 2400/0677* (2013.01); *B01L 2400/0688* (2013.01); *B01L 2400/086* (2013.01); *G01N 33/558* (2013.01); *Y10T 436/25375* (2015.01)

(58) Field of Classification Search
CPC .............................. G01N 33/50; G01N 33/537
USPC .......................................... 436/539, 538, 16
See application file for complete search history.

(56) References Cited

U.S. PATENT DOCUMENTS 8,257,562 B2    9/2012    Isaksson et al.
2002/0041831 A1    4/2002    Battrell et al.
(Continued)

FOREIGN PATENT DOCUMENTS

EP    1906167 A2    4/2008
EP    2020598 A1    2/2009

OTHER PUBLICATIONS

IB Mendel-Hartvig, "Forecast Technology—A versatile Platform for POC Testing, Amic AB/Orth Clinical Diagnostics," Oak Ridge Conference Frontiers in Clinical Diagnostics, Baltimore, USA, Ortho Clinical Diagnostics, Apr. 16, 2009, 38 pages.
(Continued)

*Primary Examiner* — Natalia Levkovich
(74) *Attorney, Agent, or Firm* — Lando & Anastasi, LLP

(57) ABSTRACT

Devices and methods are disclosed herein for separating a supernate from a suspension. The apparatus consists of a sample zone, a controllable gate, and an analysis zone. The sample zone holds the suspension. The analysis zone passively transports a supernate formed from the suspension by capillary transport. A controllable gate prevents the suspension in the sample zone from flowing into the analysis zone. The controllable gate can be triggered after the supernate has separated from the suspension to allow the supernate to flow into the analysis zone.

16 Claims, 6 Drawing Sheets

(51) Int. Cl.
  *G01N 33/49*   (2006.01)
  *B01D 21/00*   (2006.01)
  *B04B 11/04*   (2006.01)
  *B01L 3/00*    (2006.01)
  *G01N 33/558*      (2006.01)

(56) References Cited

U.S. PATENT DOCUMENTS

| | | | |
|---|---|---|---|
| 2004/0077103 A1* | 4/2004 | Buechler | B01L 3/50273 436/514 |
| 2004/0232074 A1 | 11/2004 | Peters et al. | |
| 2007/0266777 A1 | 11/2007 | Bergman et al. | |
| 2008/0073297 A1 | 3/2008 | Shiraishi et al. | |
| 2009/0208975 A1 | 8/2009 | D'Costa et al. | |
| 2012/0107851 A1 | 5/2012 | Killard et al. | |

OTHER PUBLICATIONS

Nammoonnoy et al., "Photo-Actuated Droplet Microfluids," 15th International Conference on Miniaturized Systems for Chemistry and Life Sciences, Oct. 2-6, 2011, Seattle, Washington, USA, 3 pages.

Xin et al., "Reversibly Switchable Wettability," Critical Review; Chemical Society Reviews, First Published as an Advance Article on the web Oct. 20, 2009 at www.rsc.org/csr, 14 pages.

* cited by examiner

APPARATUS AND METHOD FOR SEPARATING PLASMA FROM BLOOD AND DELAYED WETTING

CROSS-REFERENCE TO RELATED APPLICATION

This application claims priority under 35 U.S.C. §120 as a division of U.S. patent application Ser. No. 13/679,620 filed Nov. 16, 2012, titled APPARATUS AND METHOD FOR SEPARATING PLASMA FROM BLOOD AND DELAYED WETTING, which is incorporated herein by reference in its entirety for all purposes.

FIELD OF THE DISCLOSURE

In general, the disclosure relates to an apparatus for separating plasma from blood and a method for controlling transport of the separated plasma into an analysis zone using a controllable gating region.

BACKGROUND OF THE DISCLOSURE

For many diagnostic blood tests, it is required or preferable to eliminate red blood cells, white blood cells, and platelets from the patient's blood so that only the blood plasma remains for analysis. In laboratories, blood is typically segregated by centrifugation, and the plasma is siphoned and transported to the analysis instrumentation. This requires specialized instrumentation and significant energy consumption. An emerging objective in point-of-care diagnostics is to perform analysis of a patient's blood using a minimal quantity blood. This has led to the development of microfluidic devices for blood separation and blood testing. In microfluidic devices, blood may be propelled through a filter or separator and the plasma filtrate pumped into analysis chambers. Separation techniques include ultrasonic separation, dielectrophoretic separation, and mechanical size selection. These are active separation techniques which require complicated power systems and plasma transportation channels to move the separated plasma into an analysis region.

Prior passive microfluidic blood testing devices have utilized capillary flow to transport whole blood across an analysis zone. Using the whole blood, rather than just the plasma, has negatively impacted the capillary flow and, in some cases, whole blood is not suitable for analysis. Vacuum flow has also been used; however, vacuum flow devices require long-term storage of a low pressure reservoir. This complicates the fabrication process and entails a higher material cost, which makes a vacuum flow device less practical for wide-scale use.

SUMMARY OF THE DISCLOSURE

There is therefore a need for an apparatus that can both separate plasma from blood cells and transport the plasma into an observation zone without using active separation or active transport. Such an apparatus should use minimal energy and be relatively simple to fabricate. Accordingly, devices and methods are disclosed herein for separating a supernate from a suspension. The apparatus consists of a sample zone, a controllable gate, and an analysis zone. The sample zone holds the suspension. The analysis zone passively transports a supernate formed from the suspension by capillary transport. A controllable gate prevents the suspension in the sample zone from flowing into the analysis zone. The controllable gate can be triggered after the supernate has separated from the suspension to allow the supernate to flow into the analysis zone. In some embodiments, the controllable gate comprises a region coated in a convertible hydrophobic/hydrophilic material. A light source, a heat source, and an electric field can be applied to the controllable gate to trigger a transition of the controllable gate between a hydrophobic state and a hydrophilic state. The controllable gate can include a plurality of microstructures to promote passive transport of the supernate by surface tension forces when in a hydrophilic state. In some embodiments, the analysis zone comprises a plurality of microstructures for promoting the capillary transport.

In some embodiments, the controllable gate comprises one or more rows of microstructures that are coated in a convertible hydrophobic material that becomes hydrophilic when exposed to ultraviolet light. In other embodiments, the controllable gate comprises a movable barrier. The removable barrier can be removed by applying a heat source or a light source to the barrier. Alternatively, the removable barrier can be an adhesive strip.

In some embodiments, the triggering of the controllable gate causes the controllable gate to dissolve in the supernate. In some embodiments, the apparatus includes a reagent port for introducing a reagent for tagging a component of the supernate. In some embodiments, the suspension is blood. In such embodiments, the sample zone can include an anticoagulant for preventing coagulation of blood plasma of the blood.

In some embodiments, the separation of the suspension occurs by sedimentation. A reagent in the sample zone or an acoustic source directed at the sample zone can accelerate separation of the supernate from the precipitate. According to another aspect, the invention relates to methods for separating a supernate from a suspension and transporting the supernate using any of the apparatuses described above.

According to another aspect, the invention relates to a system for testing blood plasma. The system comprises a diagnostic chip, which may be similar to any of the apparatuses described above, a sensor, and a processor. The sensor is directed at the analysis zone for observing a physical property of the supernate. The processor receives data collected by the sensor and processes the received data to determine the physical property of the supernate.

In some embodiments, the system includes a display in communication with the processor for displaying the determined physical property. In some embodiments, the system includes a reagent for tagging a component of the supernate. The sensor can observe the tagged component when the component is present in the supernate. In some embodiments, the system includes a heat source, a light source, and an electric field source for applying to the removable barrier, thereby allowing the supernate to flow into the analysis zone.

In some embodiments, the system includes a separation detector directed at the sample zone for observing the purity of the supernate and outputting a signal indicative thereof. Based on the signal, the processor can selectively trigger the controllable gate to allow the supernate to flow into the analysis zone based on the received signal.

BRIEF DESCRIPTION OF THE DRAWINGS

The system and method may be better understood from the following illustrative description with reference to the following drawings in which.

DETAILED DESCRIPTION

To provide an overall understanding of the invention, certain illustrative embodiments will now be described, including devices and methods for separating plasma from blood and controlling transport of the separated plasma into an analysis zone using a controllable gating region. However, it will be understood by one of ordinary skill in the art that the systems and methods described herein may be adapted and modified as is appropriate for the application being addressed and that the systems and methods described herein may be employed in other suitable applications, and that such other additions and modifications will not depart from the scope thereof.

Figure 1A:
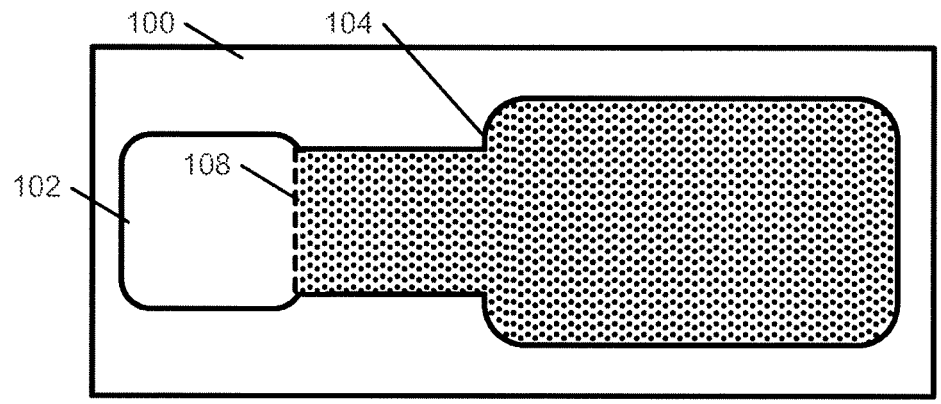
FIG. 1A is a top view of an illustrative embodiment of a plasma separation and flow apparatus having a barrier between the sample zone and the observation zone, according to an illustrative embodiment of the invention.
Figure 1B:
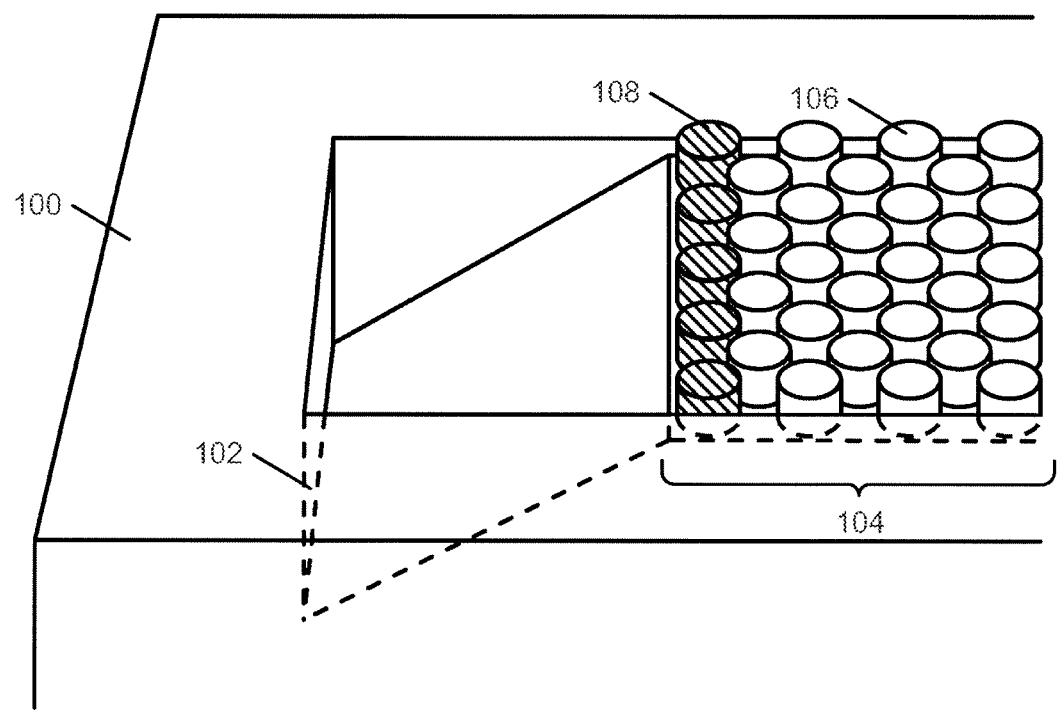
FIG. 1B is a perspective view of the plasma separation and flow apparatus shown in FIG. 1A, according to an illustrative embodiment of the invention.

An apparatus for receiving a droplet of blood in a sample zone, allowing the plasma to separate from the blood in the sample zone, and allowing the plasma to flow through an observation zone is shown in FIGS. 1A and 1B. FIG. 1A is a top view of the apparatus 100, and FIG. 1B is a perspective view a portion of the apparatus 100. The apparatus includes a sample zone 102 in which the blood droplet is placed and an observation zone 104 to the right of the sample zone 102. Only a portion of the observation zone is shown in FIG. 1B. As shown in FIG. 1B, the sample zone is a well that extends vertically deeper than the observation zone 104. When the blood droplet is placed in the sample zone 102, the blood separates by sedimentation, leaving the plasma at the top of the sample zone 102. Red blood cells, white blood cells, and platelets from the blood sample settle at the bottom of the sample zone 102 to form a precipitate that reaches a vertical height that is lower than the base of the observation zone 104. After separation, the supernatant plasma extends vertically above the base of the observation zone 104. Upon activation, the separated plasma flows rightward through the observation zone 104. The observation zone 104 contains micro-pillars, represented by dots in FIG. 1A and cylinders 106 in FIG. 1B, which cause the plasma to flow from left to right across the observation zone 104 by capillary action. The sample zone 102 is separated from the observation zone 104 by a barrier 108, represented by a dotted line in FIG. 1A and by the leftmost row of micro-pillars 106 in FIG. 1B. The barrier 108 contains the blood droplet within the sample zone 102 until the barrier 108 is triggered or removed to allow plasma to flow out of the sample zone 102 and into the observation zone 104.

Figure 2:
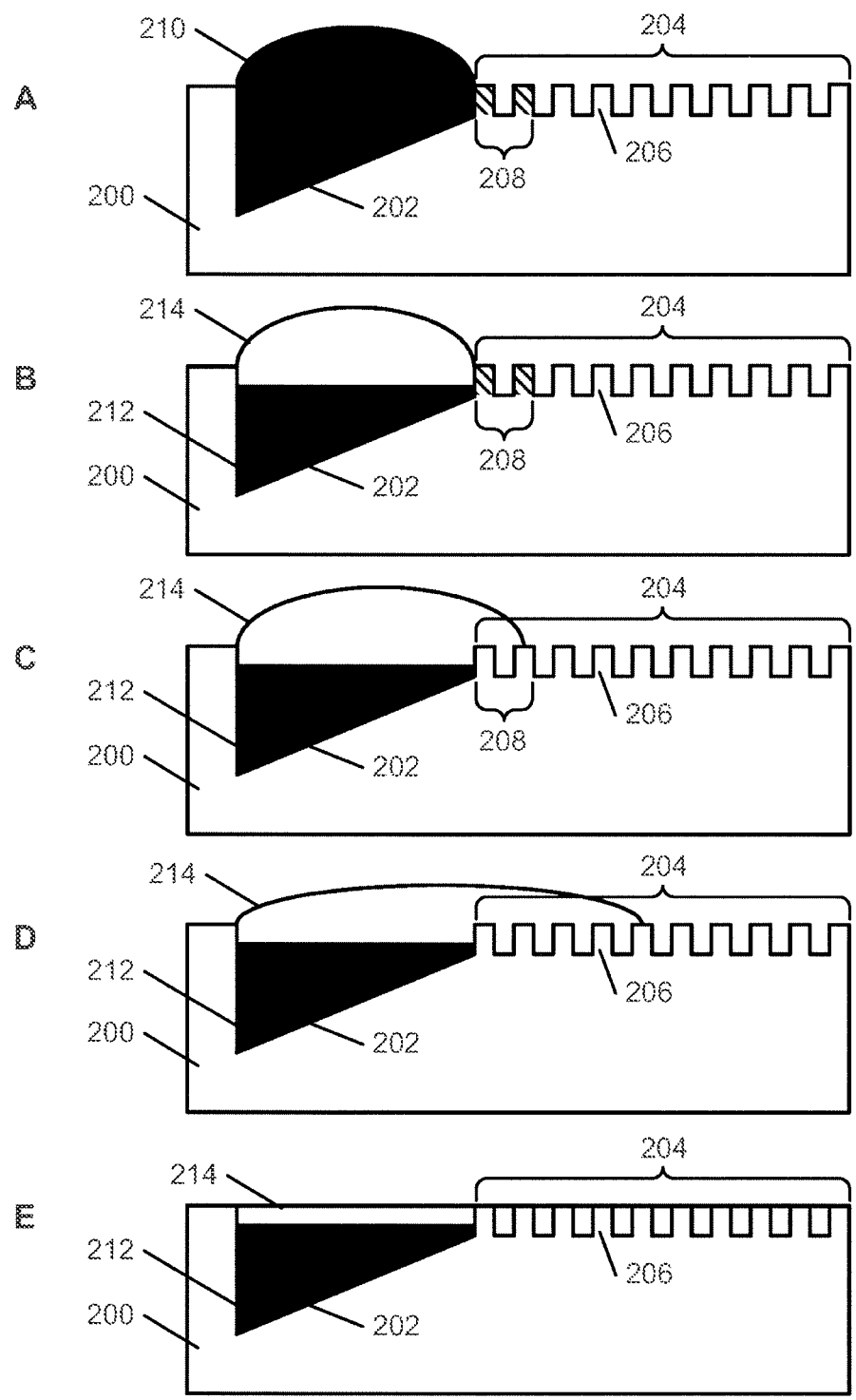
FIG. 2 is a series of diagrams illustrating a cross-section of the plasma separation and flow apparatus of FIG. 1 and a method for using the apparatus to separate plasma from blood and transport the plasma through an analysis zone, according to an illustrative embodiment of the invention.

The apparatus 100 is an assay chip which can be molded or etched from, for example, glass, a polymer, or silicon. The apparatus 100 can be formed of any material that does not react with blood or blood plasma and is suitable for molding. The topography of the apparatus 100 can be formed by, for example, hot embossing, etching, photolithography, injection molding, soft lithography, or other techniques. The sample zone 102 is sized to accept a minimum quantity of blood, e.g., 10-100 µl. As shown in FIG. 1B, the sample zone 102 is a triangular prism having an angled wall leading up to the barrier 108. This configuration of the sample zone 102 prevents the leakage of non-plasma blood components into the observation zone. Other shapes can be used for the sample zone 102, e.g., tetrahedrons, upside-down pyramids, parallelepipeds, or trapezoidal prisms. Once a blood droplet has been placed in the sample zone 102, the droplet should extend high enough vertically so that, when the barrier is triggered to allow the plasma to flow, the plasma is able to flow out of the sample zone 102 and into the observation zone 104. As shown in FIG. 2, the blood can extend vertically above the plane of the observation zone 104; the blood is retained by surface tension. The geometry of the apparatus should be designed to extract as much of the plasma from a blood droplet (which his approximately 55% plasma) of a known volume as possible without contamination by other components of blood. In some embodiments, an anticoagulant, such as heparin, ethylenediaminetetraacetic acid (EDTA), citrate, or oxalate, is stored in the apparatus 100 or placed in the sample zone 102 when the blood droplet is transferred to prevent coagulation of the plasma.

The observation zone 104 is covered by micro-pillars 106, which promote capillarity through the observation zone 104. The capillary action (a.k.a. "wicking") causes the blood plasma to flow through the observation zone 104 without any active pumping or other external forces. In FIG. 1B, the micro-pillars 106 are cylindrical; in other embodiments, the micropillars 106 have elliptical cross sections or polygonal cross sections. In some embodiments, the micro-pillars 106 taper towards their tips. In some embodiments, the micro-pillars 106 are coated in a hydrophilic material, such as dextran, to promote capillary action. The height and diameter of the micro-pillars 106 may be in the range of 1-100 µm. The flow rate of the plasma through the observation zone 104 is controlled by the distance between the micro-pillars 106. A smaller distance between micro-pillars 106 creates a higher capillary force, which causes the steady state flow rate to be slower. In addition, the longer the channel, the slower the steady flow rate will be. In some embodiments, the micro-pillars 106 create a flow rate in the range of 0.1-10 µL/min across the observation zone 104. The micro-pillars 106 are arranged in a regular formation, such as the rows shown in FIGS. 1A and 1B.

In FIG. 1A, the observation zone 104 has two regions, a narrower region towards the left and a wider region towards the right. In some embodiments, the narrower region is observed, while the wider narrower region exists to continue the flow and act as a waste chamber. In some embodiments, a reagent is added to the plasma, either in the sample zone 102 or in the observation zone 104. The plasma can be observed in the narrower region of the observation zone 104 while the reagent is added and/or in the wider region of the observation zone 104 after the reagent has been added. The observation zone 104 can consist of only one region or more than two regions, and may include two or more separate reaction zones in which different tests or duplicate tests can be carried out using a single blood droplet.

The barrier 108 may consist of one or more rows of micro-pillars 106 that resist the flow of plasma. This is shown in FIG. 1B, wherein the leftmost row of micro-pillars is shaded, indicating that they have some property differentiating them from the micro-pillars 106 in the remainder of the observation zone 104. For example, the leftmost row of micro-pillars 108 can be coated in a convertibly or reversibly wettable material that can be converted from a hydrophobic state to a hydrophilic, and may be able to reverse back to a hydrophobic state. Alternatively, the leftmost row of pillars 108 can be physically altered, e.g., made wide enough to prevent the plasma from passing through. In other embodiments, rather than an altered row of micro-pillars 108, there is a physical barrier that is not formed by micro-pillars but is situated to the left of the micro-pillars 106. For example, the physical barrier can be composed of wax or an adhesive strip that can be melted or removed, respectively. Various barriers and methods for removing the barriers are discussed further in relating to FIGS. 5 through 8.

In some embodiments, the apparatus 100 is covered. Covering the apparatus 100 makes the sample less sensitive to evaporation and decreases the likelihood of contamination. However, leaving the apparatus 100 uncovered simplifies the design and manufacturing and allows easier deposition of reagents into the observation zone 104. If a cover is used, it can include a port through which the blood droplet can be introduced and can include a window or opening so that observational equipment can image or measure the plasma.

FIG. 2 is a series of diagrams illustrating a cross-section of an apparatus 200 for plasma separation and flow that is similar to the apparatus described in relation to FIGS. 1A and 1B and a method for using the apparatus to separate plasma from blood and transport the plasma through an analysis zone. Diagram A shows a droplet of whole blood 210 placed in a sample zone 202. The blood droplet 210 extends above the boundaries of the sample zone 202 and above the observation zone 204, but is retained from spilling by surface tension. The barrier 208 further retains droplet 210 on the rightmost edge of the sample zone 202. The surface of the observation zone 204 from which the micro-pillars 206 protrude is lower than the other walls of the sample zone 204; if the barrier 208 did not retain the blood 202, it would flow to the right through the observation zone 204.

Diagram B shows the droplet of blood 210 after gravity has caused the red blood cells, white blood cells, and platelets 212 to precipitate on the bottom of the sample zone 202. The sedimentation leaves supernatant plasma 214 at the top of the droplet. It typically takes in the range of five to ten minutes for the blood cells 212 to precipitate by sedimentation. The precipitation can be accelerated by physical or chemical means. For example, an acoustic source can be directed at the blood droplet 210 to accelerate sedimentation, or a reagent, such as antibodies that bind to blood cells and cause agglutination, can be added to the blood droplet 210 to cause rapid precipitation of the blood cells 212. Other means for accelerating sedimentation or causing the isolation of the supernatant plasma 214 include thermal methods, centrifugation, application of magnetic forces and mechanical agitation. For example, a thermal means for accelerating sedimentation may include warming the apparatus 200 by a separate or integrated heater, such as an inline resistive heater at the bottom of, or surrounding the sample zone 202. Additionally, the centrifugation method may include placing the apparatus 200 in a centrifuge, such that when the apparatus is spun in the centrifuge the formed elements of the blood collect at the bottom of the sample zone 202. In some implementations, accelerating the sedimentation process by a means for applying magnetic forces includes applying a continuous magnetic field around the sample zone. The formed elements of the blood may then be drawn to or repelled from the magnet, and thus separated from the blood serum and plasma. In other embodiments, the blood is agitated by placing the apparatus 200 on a shaker table or vortexer. In some embodiments, an optical sensor is directed at the sample zone 202 to detect when the blood cells 212 have settled and the plasma 214 has fully separated out. The optical sensor may be part of the apparatus 200 or built into a diagnostic system in which the apparatus 200 is placed, which is described in detail in relation to FIG. 3. In other embodiments, a biosensor is built into the sample zone 202 or inserted into the sample zone 202 to detect whether the plasma 214 has fully separated out.

Once the blood cells 212 have precipitated from the whole blood 210, leaving the plasma 214 at the top of the droplet, the barrier 208 is triggered or removed to allow the plasma to flow into the observation zone 204. The barrier 208 is opened by, for example, a light source, a heat source, an electric field source, or a mechanical action. In one exemplary embodiment, the micro-pillars making up the barrier 208 are coated in a reversible superhydrophobic material, such as vanadium (V) oxide (V2O5) or another metal oxide nanomaterial that can be triggered to become hydrophilic. Irradiation of ultraviolet (UV) light on the V2O5 coating transforms the coating to a hydrophilic state, allowing the supernatant plasma, which is composed of approximately 93% water, to wet the barrier micro-pillars 208. Rather than a reversibly wettable metal oxide, photosensitive polymers can be used. For example, copolymers of N,N-dimethyl acrylamide and 4-phenylazophenyl acrylate turn hydrophilic and dissolve upon UV light irradiation. If this type of copolymer is used, the barrier 508 can not only coat the micro-pillars but also fill in the space between the micro-pillars, since the dissolution of the polymers will remove the copolymer from the space between the micro-pillars. Spiropyrans, particularly spiropyran nanofibers, also become reversibly wettable when irradiated by UV light. Other copolymers, such as copolymers of N,N-dimethyl acrylamide and N-4-phenylazophenyl acrylamide, are hydrophobic when irradiated by UV light and become hydrophilic at the removal of the light. If such a copolymer if used, the barrier 208 is irradiated with UV light until separation has occurred, at which point the UV light is turned off. Alternative barrier materials and methods for triggering or removing the barrier 208 are discussed further in relation to FIGS. 5 through 8.

Once the barrier 208 has been opened, the plasma begins to flow rightward, as shown in Diagrams C and D. The plasma 214 flattens out as it flows, so that in Diagram E, the plasma has flowed and flattened to cover the entire observation zone 204 at the height of the micropillars 206. If the observation zone 204 extends further to the right, capillary action causes the plasma to continue flowing out of the sample zone 202 and further into the observation zone 204.

Diagrams C and D show the plasma flowing over the tops of the micro-pillars 206. In this embodiment, the observation zone 204 should be configured to prevent the plasma from spilling out over the sides, e.g., by having a higher side wall than is shown in FIG. 1B or by placing a hydrophobic barrier at the sides of the observation zone 204. In other embodiments, the plasma is able to flow between the micro-pillars 206, but not over the micro-pillars. To create this type of flow, the tops of the micro-pillars 206, but not the sides, can be hydrophobic. Alternatively, a cover can be placed over the observation zone 204 that physically prevents flow above the micro-pillars 206.

Figure 3:
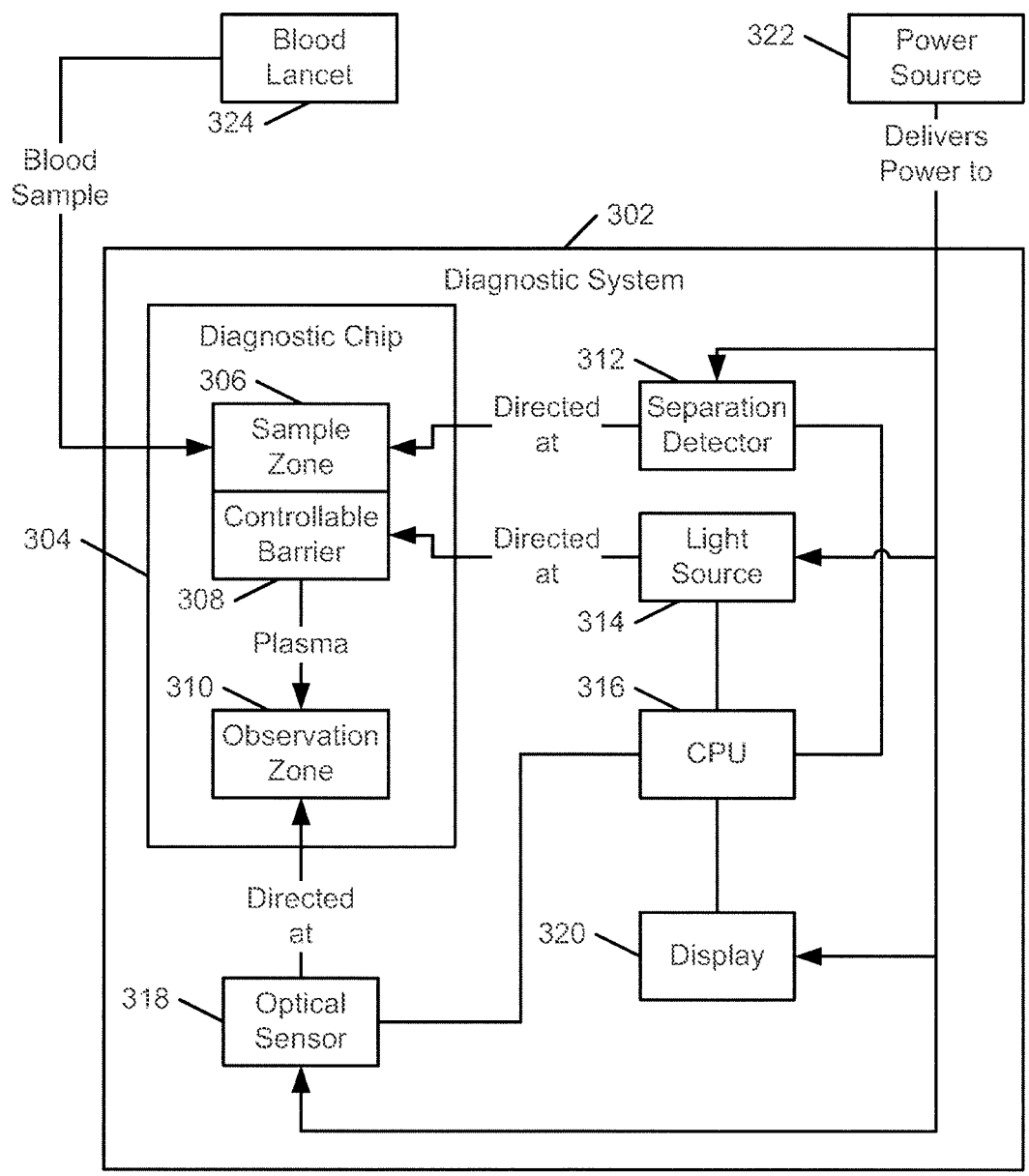
FIG. 3 is a block diagram of a diagnostic system for use with the plasma separation and flow apparatus of FIG. 1, according to an illustrative embodiment of the invention.

FIG. 3 is a block diagram of a system 300 testing blood plasma. The system consists of a diagnostic system 302, an external power source 322, and a blood lancet 324. The diagnostic system 302 includes of a removable diagnostic chip 304, which is similar to the apparatuses 100 and 200 discussed in relation to FIGS. 1A, 1B, and 2. The diagnostic system 304 also includes a separation detector 312, a light source 314, an optical sensor 318, a central processing unit (CPU) 316, and a display 320.

The diagnostic chip 304 includes a sample zone 306, which is similar to the sample zones 102 and 202 described in relation to FIGS. 1A, 1B, and 2; a controllable barrier 308, which is similar to any of the barriers 108 and 208 described in relation to FIGS. 1A, 1B, and 2; and an observation zone 310, which is similar to the observation zones 104 and 204 described in relation to FIGS. 1A, 1B, and 2. As previously described, a blood droplet is introduced in to the sample zone 306 of the diagnostic chip and, after sedimentation and/or other methods have left the supernatant plasma at the top of the droplet, the controllable barrier 308 allows the plasma to flow into the observation zone 310. The diagnostic chip 304 is removable and replaceable, and the diagnostic system 302 has a mounting system or is otherwise configured to receive and position a diagnostic chip 304. In some embodiments, the diagnostic chip 304 has one or more reference spots that can be detected by a reader to help align the diagnostic chip 304 in the diagnostic system 302. The diagnostic chip 304 can either be disposable or reusable if treated, e.g., by autoclaving, to avoid cross-contamination. The diagnostic chip 304 can receive a blood sample either outside of the diagnostic system 302 or after the chip has been inserted into the diagnostic system 302. In some embodiments, the diagnostic system 302 has a plurality of diagnostic chip ports for testing a plurality of diagnostic chips 304 at once.

In some embodiments, the observation zone 310 and/or sample zone 306 have one or more reagent ports for introducing a reagent to react with the plasma. Under a given condition of the plasma, a particular reagent forms a particular conjugate or has some other effect on the blood plasma that can be detected in analysis. For example, a reagent can be added that forms a conjugate with a particular antibody to detect the presence of the antibody in the blood droplet. In some embodiments, the reagent is a dye that tags antibodies and can be optically detected. If a reagent is stored on the diagnostic chip 304, the conditions for storing the diagnostic chip 304 may be more limited than if the reagent is added by the diagnostic system 302 during analysis of the blood droplet. Additionally, adding the reagent during the analysis would make the diagnostic chips 304 more versatile. However, storing the reagent on the diagnostic chip 304 can simplify the design of both the diagnostic system 302 and the diagnostic chip 304. If the reagent is stored on the diagnostic chip 304, it can be stored in the sample zone 306, in the observation zone 310, or in another chamber from which it flows towards the plasma when triggered. If stored in another chamber, the same mechanism used for triggering the controllable barrier 308 to allow the flow of plasma can be used to trigger the release of the reagent. If the reagent is a water-based liquid stored in the observation zone 310, the controllable barrier 308 would prevent the reagent from passing into the sample zone 306.

After a blood droplet is introduced to the sample zone 306, the blood droplet is retained in the sample zone 306 until the plasma has sufficiently separated from the blood cells. The separation detector 312 is directed at the sample zone 306 for determining when the plasma is sufficiently separated from the blood cells in the blood droplet. The separation detector 312 may be an optical sensor directed at the sample zone 306 to detect when the blood cells 212 have settled and the plasma 214 has fully separated out. In other embodiments, the separation detector 312 is a biosensor for determining the biological makeup of a region of the sample zone. The separation detector 312 may be directed near or slightly above the expected boundary between the supernatant plasma and the precipitated blood cells, or there may be a plurality of separation detector 312 directed around the expected boundary. The separation detector 312 can be part of the apparatus 200 or built into a diagnostic system in which the apparatus 200 is placed. In some embodiments, the separation detector 312 is a biosensor that is inserted into the sample zone 306. In this embodiment, the separation detector 312 can either be disposed of after a single use or cleaned between uses to prevent contamination.

Once the plasma has sufficiently separated from the blood cells, light source 314 triggers the hydrophobic barrier 308 by shining UV light onto the barrier 308. The UV light causes the coating to become hydrophilic, allowing the plasma to wet the barrier 308 and flow into the observation zone 310, as described above in relation to FIG. 2. As the plasma flows through the observation zone 310, one or more optical sensors 318, which are directed at the observation zone 310, measure physical properties of the plasma, such as fluorescence or the presence of other dyes tagged to antibodies in the plasma. The optical sensors 318 can be, for example, charged-coupled devices (CCDs), photomultipliers, or photodiodes. The optical sensors 318 may be coupled to a light source that is directed at the observation zone 310. If the diagnostic chip 304 is formed of a transparent material, one or more optical sensors 318 can be positioned to observe the plasma through the walls of the observation zone 310. Alternatively or additionally, one or more optical sensors 318 can be positioned above the observation zone 310. If the diagnostic chip 304 is covered, the cover can contain one or more openings or windows through which the sensor and/or light source are directed. In other embodiments, chemical sensors, biosensors, or other types of sensors are used instead of or in addition to optical sensors 318.

The CPU 316 controls the actions of the separation detector 312, light source 314, and optical sensor 318. The CPU 316 receives signals from the separation detector 312 indicating the extent to which the supernatant plasma is free of any other blood components and compares the measured purity of the plasma to a threshold level. If the CPU 316 determines that the blood droplet has sufficiently separated into precipitate and supernatant plasma, the CPU instructs the light source 314 to turn on to trigger the controllable barrier 308 to become hydrophilic, allowing the plasma to wet the barrier 308 and pass into the observation zone 310. When the plasma flow commences, the CPU 316 instructs the optical sensor 318 to observe the plasma in the observation zone 310. The CPU 316 also receives measurements from the optical sensor 318 and processes the measurements to determine properties or diagnoses of the received blood sample.

The CPU 316 controls a display 320 that provides information to a user, such as a medical professional or technician performing the test. The display 320 outputs, for example, the type of test being performed, parameters of the test being performed, and the test results. The diagnostic device 302 can be configured to allow the user to toggle between display modes and toggle between measurement units. In some embodiments, the display 320 is a touch-screen display that can accept input from a user. The touch-screen display can be configured to receive various input from a user, who would likely be a medical professional trained in using the device. User input can include, for example, an identification of a test to be performed, testing parameters, patient information used in analysis of the data (e.g., gender, age, presence of disease, or other relevant physical characteristics), preferences for type and format of data output, a request that the results be printed, and a request that the results be sent to another person, system, or device. In other embodiments, the diagnostic system 302 includes or is connected to other user input devices for controlling the system, e.g., a keyboard, a mouse, a trackpad, a microphone, or any other user input devices known in the art.

The external power source 322 is connected to the diagnostic system 302 through a single port, such as an outlet, for delivering power to the various power-drawing components of the diagnostic system 302. In other embodiments, an internal power source such as a battery is used to power the diagnostic system 302.

The blood droplet tested by the diagnostic system 302 can be obtained using a blood lancet 324. The blood lancet 324 punctures a patient's skin to obtain a droplet of blood. An output port of the blood lancet 324 can be sized to fit in a port on the diagnostic chip 304 or the diagnostic system 302 through which the blood droplet is introduced.

Figure 4:
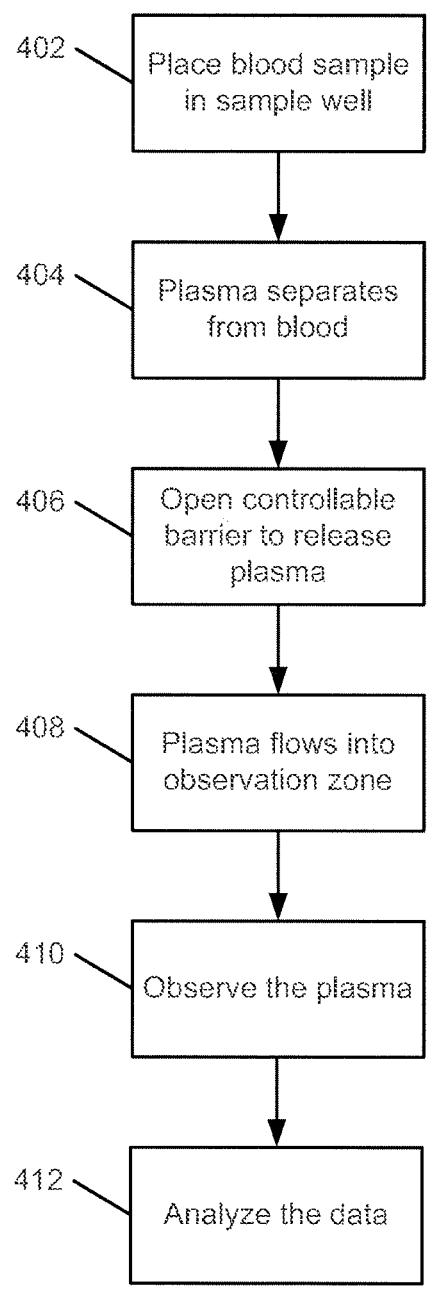
FIG. 4 is a flowchart for a method of passively separating blood plasma from blood, transporting the plasma into an observation zone, and observing the plasma, according to an illustrative embodiment of the invention.

A flowchart of a method of using the diagnostic system 302 for passively separating blood plasma from blood cells, transporting the plasma into an observation zone, and analyzing the plasma is shown in FIG. 4. First, a blood sample, retrieved from blood lancet 324, is placed into the sample well 306 (step 402). The blood plasma then separates from the rest of the blood components so that the blood cells form a precipitate and the blood plasma forms a supernate (step 404). This separation is monitored by the CPU 316 using the separation detector 312. The separation should be more complete for some tests than for others. For example, for a test in which extraneous blood cells affect the test results, the separation should be more complete than for a test in which contamination by other blood components does not affect the test results but only affects the flow through the observation zone 310. In other words, in some cases, a minimal amount of contamination by blood cells may be acceptable. If the test does not require complete separation, the acceptable amount of contamination also depends on the flow characteristics of the observation zone 310. Thus, the completeness of blood separation, and, therefore, the time between the introduction of the blood droplet to the sample zone 306 and the removal of the barrier 308, can be shorter for some tests and for some observation zone flow characteristics than for others. In some embodiments, rather than using the separation detector 312 to determine the separation of the blood components, the diagnostic system 302 has a timer and, after a measured period of time, the barrier 308 is triggered or removed. In other embodiments, a medical professional or technician monitors the readout from the separation sensor 312 on the display 320 or a timer to determine when to trigger or remove the barrier 308.

Once the CPU 316 or the medical professional or technician determines that the plasma has sufficiently separated from the other blood components, the controllable barrier 308 is triggered to open and release the plasma into the observation zone 310 (step 406). For example, the CPU 316 sends an instruction to the light source 314 to shine UV light onto the reversible superhydrophobic/hydrophilic barrier 308, at which the light source 314 is directed. The UV light makes the controllable barrier 308 hydrophilic, which allows the plasma to wet the posts of the controllable barrier 308 and flow past the barrier 308 and into the observation zone 310 (step 408). As discussed above in relation to FIG. 3, either while the plasma is in the sample zone 306 or as the plasma flows into the observation zone 310, a reagent can be introduced to the blood droplet or the blood plasma.

As the plasma flows into the observation zone, the one or more optical sensors 318 detect fluorescence, color, density, or other features of the plasma flowing through the observation zone 310 (step 410). The optical sensors 318 send the detected data to the CPU 316 which processes the data to analyze the plasma (step 412). For example, if antibodies in the plasma form fluorescent conjugates with a reagent, the level of fluorescence can be determined to identify the level of the antibodies in the patient's blood. In some embodiments, the CPU 316 compares the results of the analysis to a threshold value stored in memory to make a diagnosis of an infection or blood condition. The threshold value may depend on patient data, such as the patient's gender, age, known diseases, or other physical conditions. The measurements and/or diagnostics are shown to the user by the display 320, sent via a communication channel to another device for further processing or review, or output in another manner known in the art. In addition to providing measurement results, images of the observation channel can be recorded by the optical sensors 318, and the images can be output, for example, to the display 320.

In addition to the reversible superhydrophobic/hydrophilic barrier triggered by UV light discussed above, other barriers can be used to retain the blood droplet until the plasma has separated from the other blood components. Alternative barrier implementations include heat-triggered convertible or reversible hydrophobic barriers, electric field-triggered convertible or reversible hydrophobic barriers, removable physical barriers, and shape-memory metal barriers. Illustrative embodiments of these alternative barriers are shown in FIGS. 5 through 8 and described in further detail below. The apparatuses described in relation to FIGS. 5 through 8 can be used with the diagnostic system 302 described in relation to FIG. 3 with minor adjustments to the diagnostic system 302.

Figure 5:
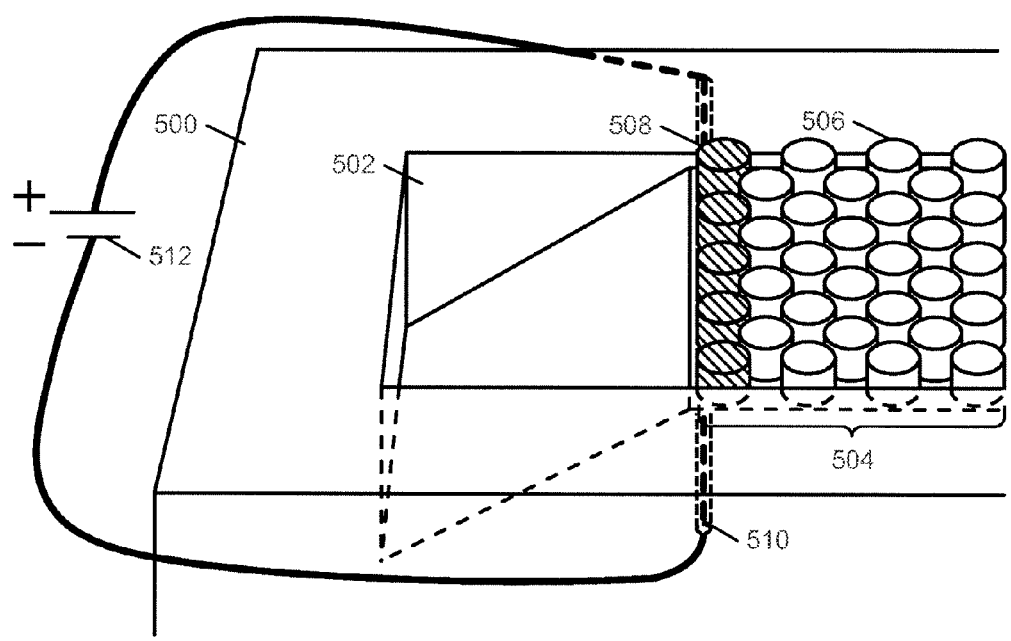
FIG. 5 is a perspective view of an illustrative embodiment of a plasma separation and flow apparatus having a heat source that can apply heat to the barrier between the sample zone and the observation zone, according to an illustrative embodiment of the invention.

FIG. 5 is a perspective view of an apparatus 500 having a heat-controlled barrier 508 between the sample zone 502 and the observation zone 504. The left-most row of micropillars 506 are coated in a heat-sensitive material that is hydrophobic at room temperature and becomes hydrophilic when heated. Alternatively, some heat-sensitive materials are hydrophilic at room temperature and become hydrophobic when heated. Thus, heating the barrier 508 allows the plasma to wet the micro-pillars 506 and pass into the observation zone 504 by capillary action. The barrier 508 can be heated by a resistive heating element 510 such as a wire that passes underneath the barrier (as shown in FIG. 5), above the barrier, or through the barrier. In some embodiments, there are multiple heat sources, e.g., heat sources above and below the barrier. The resistive heating element 510 is heated by a voltage supply such as battery 512. A processor, such as the CPU 316 described in relation to FIG. 3, is in communication with the battery 512 to turn it on and off. The battery 512 can be built into the apparatus 500 or the diagnostic system 302 can supply the voltage. If the voltage is supplied by the diagnostic system 302, the apparatus 502 can have one or more connections or electrical contacts to receive power from the diagnostic system 302.

Suitable heat-sensitive reversible hydrophobic materials include polymerized Nisopropylacrylamide (PNIPAAm), which is hydrophilic below a temperature of around 32° C. and hydrophobic above a temperature of around 32° C. For PNIPAAm, the barrier 508 is heated until the plasma has sufficiently separated, at which point the heat is removed so that the barrier 508 cools to below 32° C. In some embodiments, the apparatus 500 or the diagnostic system 302 includes a temperature controller that monitors the temperature of the barrier and applies a voltage as necessary to maintain but not exceed the temperature needed for a hydrophobic or hydrophilic barrier. In some embodiments, the temperature controller can cool the barrier 508 to speed up the transition between hydrophobic and hydrophilic.

Figure 6:
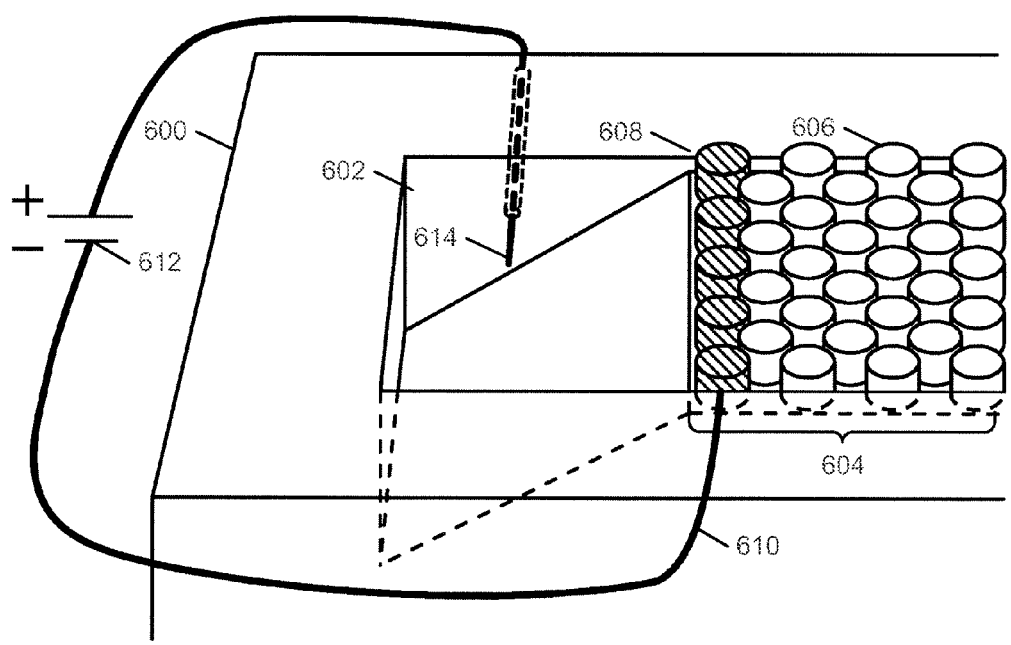
FIG. 6 is a perspective view of an illustrative embodiment of a plasma separation and flow apparatus having an electric field source that can apply an electric field between a plasma sample and a barrier between the sample zone and the observation zone, according to an illustrative embodiment of the invention.

FIG. 6 is a perspective view of an apparatus having an electric field source that can apply an electric field between a plasma sample and a barrier 608 between the sample zone 602 and the observation zone 604. FIG. 6 is similar to FIG. 5, except that the resistive heating element 510 is replaced with a pair of electrodes 610 and 614 for applying a voltage difference between the barrier 608 and the sample zone 602. When the blood sample is introduced into the sample zone 602, the electrode 614 is in contact with the blood sample. After the plasma has separated from the other blood components, the voltage supply 612 is turned on to create a voltage difference between the plasma and the barrier 608. This voltage difference induces an electric field. The electric field modifies the wetting properties of the coating to allow the plasma to wet the micro-pillars; this behavior is known as electrowetting. Suitable materials for electrowetting include amorphous fluoropolymers such as FLUOROPEL polymers, CYTOP, and Teflon AF.

Convertible or reversible hydrophobic/hydrophilic coatings, including those described in relation to FIGS. 3, 5 and 6, can be applied by deposition. For example, the coatings can be vaporized in a plasma reactor and deposited directly onto the micro-pillars of the apparatus. Alternatively, the specific micro-pillars that are used to form the barrier can be treated with argon plasma, coated with the desired convertible or reversible hydrophobic material, and further treated with argon plasma.

In addition to photosensitive, heat sensitive, and electric-field sensitive materials described above, other convertible or reversible hydrophobic/hydrophilic materials can be similarly triggered, for example, by changes in pH or by illumination by X-rays. Further detail about types of surface coatings and methods for applying the coatings is described in "Reversibly switchable wettability" by Xin and Hao, published in Chem. Soc, Rev., 2010, 39, 769-782, incorporated herein by reference. Any other coating or method known in the art for creating a wettable barrier that would not contaminate blood plasma can be used with the apparatuses described herein.

Figure 7:
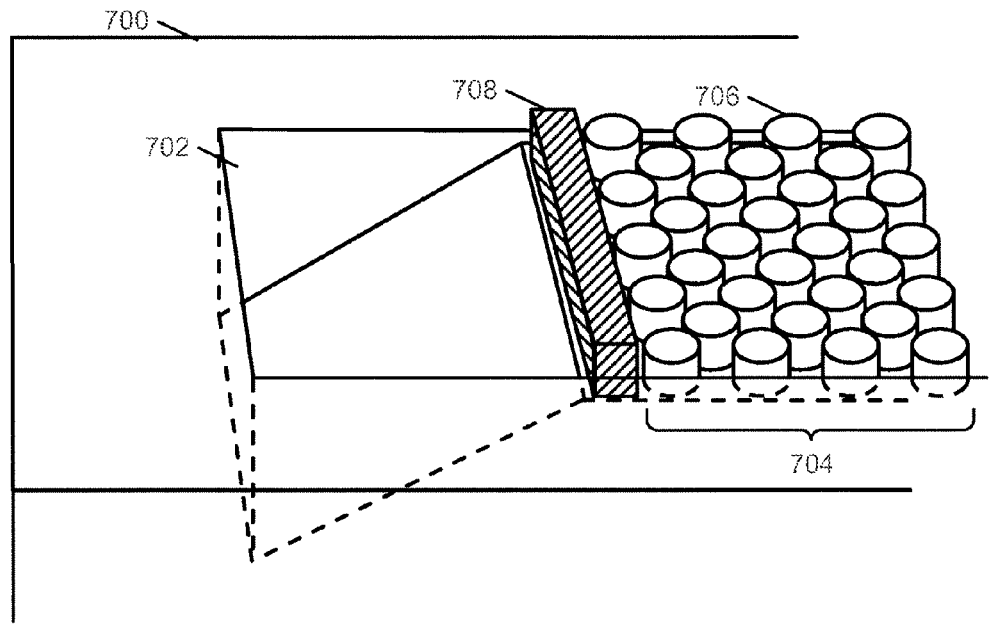
FIG. 7 is a perspective view of an illustrative embodiment of a plasma separation and flow apparatus having physical barrier between the sample zone and the observation zone, according to an illustrative embodiment of the invention.

FIG. 7 is a perspective view of an illustrative embodiment of a plasma separation and flow apparatus having physical barrier 708 between the sample zone 702 and the observation zone 704. Rather than using a hydrophobic barrier to resist the flow of the blood before separation, a physical blockade can be used to keep the blood droplet out of the observation zone 704 until after separation. The physical barrier 708 can be, for example, an adhesive strip that can be automatically removed by the diagnostic system 302 or manually removed by a medical professional or technician using the diagnostic system 302. In other embodiments, the physical barrier 708 is a wax strip that can be melted by a heat source such as the resistive heating element 510 described in relation to FIG. 5. In other embodiments, the physical barrier 708 is a material that can be dissolved by the plasma upon applying a stimulus, such as light or heat.

Figure 8:
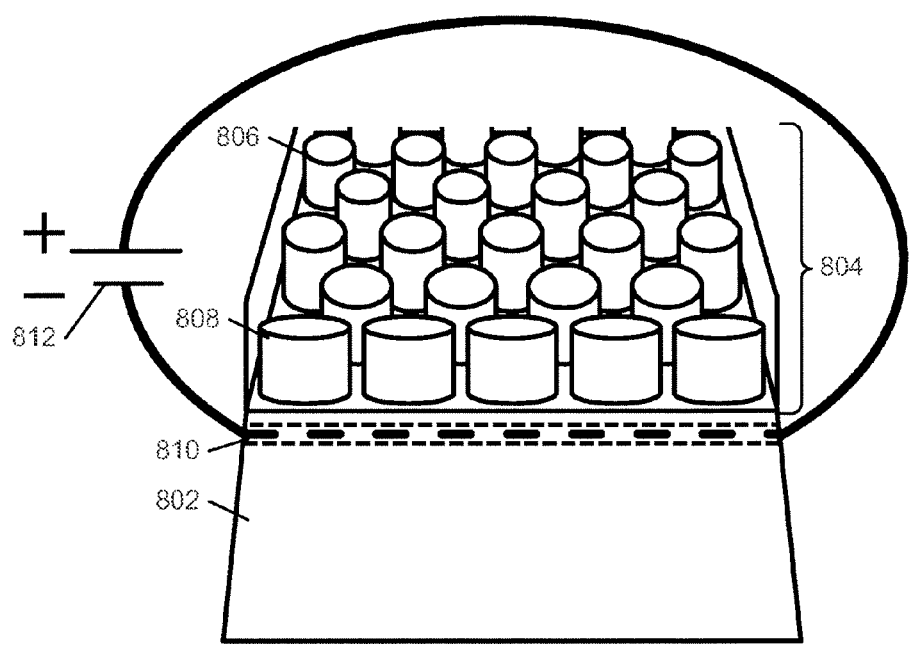
FIG. 8 is a perspective view of an illustrative embodiment of a plasma separation and flow apparatus having a heat source for controlling a barrier between the sample zone and the observation zone formed by shape-memory metal, according to an illustrative embodiment of the invention.

FIG. 8 is a perspective view of an apparatus having a barrier formed of shape-memory metal between the sample zone 802 and the observation zone 804. The shape of the shape-memory metal is controlled by a heat source 810, which is similar to the resistive heating element 510 that was described in relation to FIG. 5. The barrier consists of micro-pillars 808 that are similar to the micro-pillars 806 behind it, but the micro-pillars 808 that form the barrier are elongated so that the distance between the micro-pillars 808 is greatly reduced compared to the distance between the micro-pillars 806. When the apparatus 800 is fabricated, the micropillars 808 initially have the shape of the micro-pillars 806, but, after fabrication, they are reversibly deformed by flattening them out as shown in FIG. 8. The flattened micro-pillars 808 block the flow of blood because the distance between the micro-pillars 808 is too small for the blood to pass. Heating the micro-pillars 808 returns them to their original cylindrical shape, at which point the plasma can pass through the enlarged distance between the micro-pillars 808.

Suitable shape-memory metals include copper-zinc-aluminum-nickel, copper-aluminum-nickel, and nickel-titanium alloys. Any other type of material that can change form from a configuration that would block flow to a configuration that would enable flow can be used. For example, a barrier may have a pore size that can be enlarged upon the application of a stimulus such as heat, so that heating the barrier enlarges the pore size, which allows plasma to pass through.

While preferable embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for separating a supernate from a suspension and transporting the supernate, the method comprising:
holding the suspension in a sample zone;

preventing the suspension in the sample zone from flowing into an observation zone by a controllable barrier, the controllable barrier separating the sample zone from the observation zone;

detecting, by a separation detector, separation of a supernate from the suspension in the sample zone;

generating a detection signal after the supernate has separated from the suspension;

sending the detection signal to a controller;

triggering, by the controller, the controllable barrier after the detection signal has been received by the controller, thereby allowing the supernate to passively flow into the observation zone; and promoting, by capillary transport, the flow of the supernate through the observation zone.

2. The method of claim 1, wherein the controllable barrier comprises a region coated in a convertible hydrophobic/hydrophilic material.

3. The method of claim 2, wherein the triggering of the controllable barrier comprises applying a light source to the controllable barrier to transition the controllable barrier between a hydrophobic state and a hydrophilic state.

4. The method of claim 2, wherein the controllable barrier comprises a plurality of microstructures to promote passive transport of the supernate by surface tension forces when in a hydrophilic state.

5. The method of claim 1, wherein one or more rows of microstructures are coated in a convertible hydrophobic material, and the triggering of the controllable barrier comprises exposing one or more of the rows of microstructures to ultraviolet light that transforms the material to a hydrophilic state.

6. The method of claim 1, wherein the controllable barrier comprises a removable barrier.

7. The method of claim 6, wherein the triggering of the controllable barrier comprises removing the removable barrier by applying one of a heat source and a light source to the removable barrier.

8. The method of claim 6, wherein the removable barrier comprises an adhesive strip.

9. The method of claim 1, wherein the triggering of the controllable barrier comprises causing the controllable barrier to dissolve in the supernate.

10. The method of claim 1, wherein the observation zone comprises a plurality of microstructures for promoting the capillary transport.

11. The method of claim 1, further comprising introducing to the supernate a reagent for tagging a component of the supernate.

12. The method of claim 1, wherein the suspension comprises blood.

13. The method of claim 12, further comprising adding an anticoagulant to the blood for preventing coagulation of blood plasma of the blood.

14. The method of claim 1, wherein the separation of the suspension occurs by sedimentation.

15. The method of claim 1, further comprising at least one means for accelerating the separation of the supernate from the precipitate in the sample zone.

16. The method of claim 15, wherein the means for accelerating the separation of the supernate from the precipitate in the sample zone includes one of a means for centrifuging the suspension, a means for heating the suspension, a means for applying a magnetic force to the suspension, and a means for mechanically agitating the suspension.

* * * * *